US00PP16896P2

(12) United States Plant Patent
Kawashima

(10) Patent No.: US PP16,896 P2
(45) Date of Patent: Jul. 25, 2006

(54) ***OSTEOSPERMUM* PLANT NAMED 'KAKEGAWA AU18'**

(50) Latin Name: *Osteospermum hybrida*
Varietal Denomination: Kakegawa AU18

(75) Inventor: Moriya Kawashima, Matsumoto (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 11/054,767

(22) Filed: Feb. 10, 2005

(51) Int. Cl.
*A01H 5/00* (2006.01)

(52) U.S. Cl. ..... Plt./360

(58) Field of Classification Search ..... Plt./360
See application file for complete search history.

*Primary Examiner*—Kent Bell
(74) *Attorney, Agent, or Firm*—Jondle & Associates P.C.

(57) ABSTRACT

An *Osteospermum* cultivar particularly distinguished by its cream/ivory picotee ray floret, upright, compact growth habit, and ability to flower in hot temperatures is disclosed.

1 Drawing Sheet

Genus and species: *Osteospermum hybrida.*
Variety denomination: 'Kakegawa AU18'.

BACKGROUND OF THE NEW PLANT

'Kakegawa AU18' originated from a hybridization between *Osteospermum* 'Brightside' (U.S. Plant Pat. No. 10,596) and an unnamed *Osteospermum* breeding line (unpatented) of unknown origin in Misato, Japan. 'Brightside' was chosen for its ability to flower under short-day conditions. In 2001, the two *Osteospermum* lines were crossed and embryo rescue was performed in order to obtain viable offspring. Ten $F_1$ plants were obtained using this technique.

The $F_1$ plants were evaluated in Misato, Japan in 2002. Criteria for selection included compact growth habit, ability to bloom under short-day, warm conditions, white flower color and basal branching. In 2002, one single-plant selection was made based on the above criteria and vegetatively propagated. The selection subsequently was named 'Kakegawa AU18' and found to reproduce true to type in successive generations of asexual propagation.

DESCRIPTION OF PHOTOGRAPHS

This new *Osteospermum* plant is illustrated by the accompanying photographs which show the plant's form, foliage and inflorescences. The colors shown are as true as can be reasonably obtained by conventional photographic procedures.

DESCRIPTION OF THE NEW CULTIVAR

Figure 1:
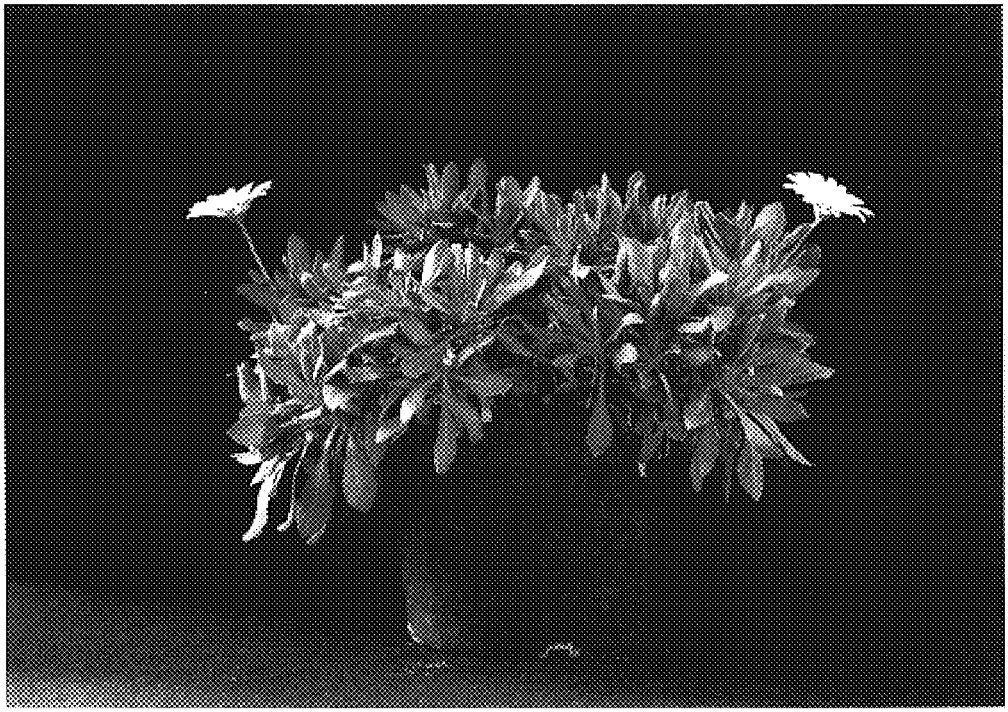
FIG. 1 shows overall plant habit.
Figure 2:
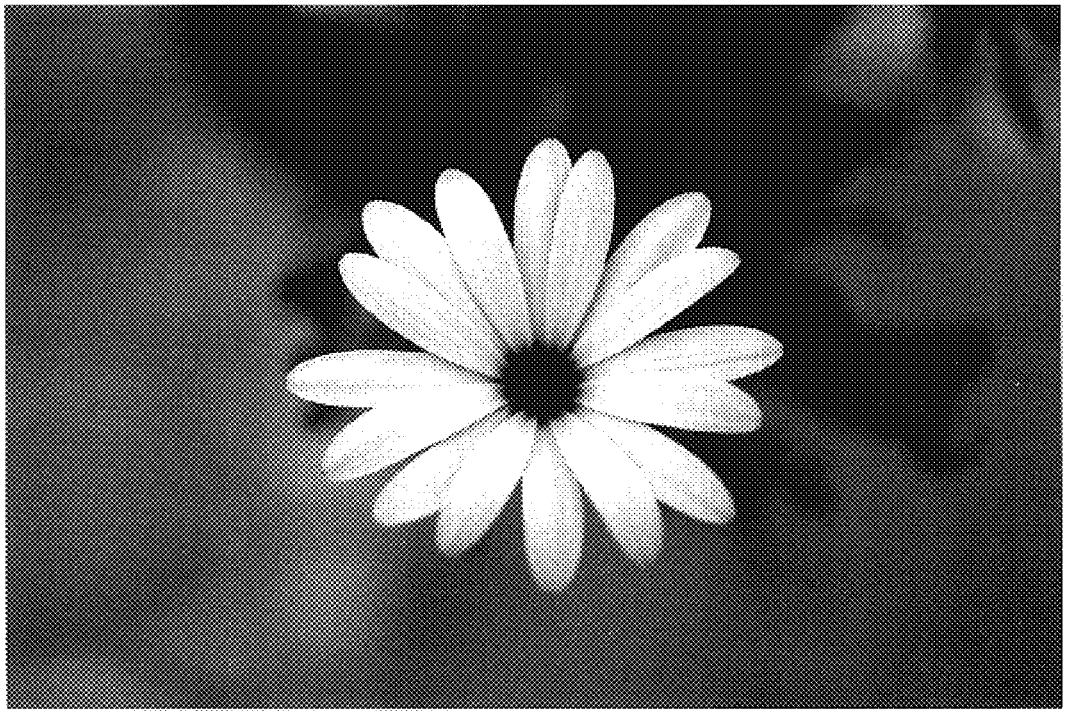
FIG. 2 shows the mature inflorescence.

The following detailed descriptions set forth the distinctive characteristics of 'Kakegawa AU18'. The data which define these characteristics were collected from asexual reproductions carried out in Salinas, Calif. Data was collected on plants grown approximately four months from transplanting rooted cuttings into 6-inch pots under greenhouse conditions in Salinas, Calif. Color references are to The R.H.S. Colour Chart of The Royal Horticultural Society of London (R.H.S.).

DESCRIPTION OF THE NEW PLANT

Classification:
*Family.*—Compositae.
*Botanical.*—*Osteospermum hybrida.*

Growth:
*Time to produce a rooted cutting.*—Cuttings will colonize a 2.5 cm diameter by 2.5 cm tall greenhouse tray cell with peat-based plant media in approximately four weeks. Cuttings are dipped in a normal dilution (1:9) of DIP 'N GROW root-inducing solution in water. The trays are misted hourly during rooting.
*Environmental conditions for plant growth.*—Rooted cuttings are transplanted to pots with a 16 cm diameter, one plant per pot. Peat-based growing media is used. The pots are watered using a 150–200 ppm fertilizer solution containing 18% nitrogen, 8% phosphorus and 18% potassium. The soil is allowed to dry between waterings. During the first few weeks after transplanting, the plants were grown under evening temperatures around 15–18° C. for good root growth. When plants reached 7.5–10 cm in height they were pinched back to 5–6 leaves to promote branching. Spring and summer daytime high temperatures in Salinas, Calif., where the data was collected, range from 16–25° C.
*Time to bloom from propagation.*—Approximately four weeks when rooted vegetative cuttings are transferred to a 16 cm. diameter pot. Flowering season is all year in the United States. Vernalization is not required to induce flowering.

Plant description:
*Habit.*—Upright, compact.
*Life cycle.*—Perennial.
*Form.*—Freely branching with many lateral branches.
*Height.*—20 cm.
*Width.*—35 cm.

Stems:
*Internode length.*—0.4–1.0 cm.
*Stem description.*—Ancipital, woody.

*Stem diameter.*—0.5–0.7 cm.
*Stem color.*—RHS 144B (green).
*Pubescence.*—Slight.
*Pubescence shape.*—Linear.
*Pubescence color.*—RHS 155A (white).

Leaves:
*Arrangement.*—Alternate.
*Shape.*—Obovate to oblanceolate.
*Apex.*—Mucronate.
*Base.*—Decurrent.
*Margin.*—Serrate.
*Venation.*—Pinnate.
*Surface.*—Dull, smooth.
*Surface pubescence.*—Slight.
*Length.*—4.0–4.5 cm.
*Width.*—1.5–1.8 cm.
*Thickness.*—0.1 cm.
*Color.*—Upper surface: RHS 147A (green). Lower surface: RHS 147B (green).
*Venation color.*—Upper surface: RHS 144A (green). Lower surface: RHS 143C (yellow-green).
*Petiole length.*—3.1 cm–5.2 cm.
*Petiole diameter.*—0.2 cm.
*Petiole color.*—RHS 144A (yellow-green).

Inflorescence:
*Type.*—Capitulum (head); disc florets are perfect and ray florets are carpellate.
*Flowering habit.*—Determinate.
*Lastingness of inflorescences.*—3–4 days on the plant.
*Fragrance.*—None.
*Seed production.*—None observed.
*Diameter.*—5.5–7.0 cm.
*Depth.*—1.5–3.0 cm.
*Disc diameter.*—1.0–1.5 cm.
*Disc floret number.*—90–100.
*Peduncle length.*—7.0 cm.
*Peduncle diameter.*—0.2 cm.
*Peduncle color.*—RHS 144A (green).
*Peduncle texture.*—Dull, slight pubescence.
*Phyllaries.*—Arrangement: Symmetrical. Length: 1.4 cm. Width: 0.1–0.2 cm. Apex: Acute. Margin: Entire. Shape: Lanceolate. Color: Upper surface: RHS 144A (green). Lower surface: RHS 144A (green) with RHS 79 (purple) center portion.

Ray florets (ligules):
*Corolla.*—One ray per ray floret; only the outer row of florets are the ray florets.
*Number of ray florets per inflorescence.*—22.
*Ray floret length.*—3.4–4.0 cm.
*Ray floret width.*—0.5–0.7 cm.
*Ray floret shape.*—Spatulate.
*Ray floret apex.*—Acute.
*Ray floret margin.*—Entire.
*Ray floret color.*—Upper surface: RHS 155D (white). Lower surface: RHS 155A (white) at edge of petal; RHS 160C (grayed-white) center portion.
*Ray floret pubescence.*—Glabrous.
*Ovary.*—Superior.
*Pistil form.*—One style with two stigma branches.
*Pistil length.*—0.4 cm.
*Stigma color.*—RHS 77A (purple).
*Style color.*—RHS 77A (purple).

Disc florets:
*Disc floret number per inflorescence.*—70–80.
*Disc floret color (both surfaces).*—RHS N77A (purple) at the tip fading to translucent at base.
*Disc floret shape.*—Ensiform.
*Disc floret apex.*—Acute.
*Disc floret base.*—Cuneate.
*Disc floret margin.*—Entire.
*Disc floret size.*—Length: 0.5 cm. Width: less than 0.1 cm.
*Pistil form.*—One style with two stigma branches.
*Ovary.*—Superior.
*Style color.*—Translucent.
*Stigma color.*—RHS 92A (violet-blue).
*Stamens.*—5, fused into a single tube.
*Location of gynoecium.*—On both ray florets and disc florets.
*Anther color.*—RHS 12C (yellow).
*Pollen color.*—RHS 28A (orange).
*Location of androecium.*—On disc florets only.

Disease and insect resistance: Very disease resistant, however, plants are susceptible to aphids, thrips, whiteflies and worms.

COMPARISION WITH KNOWN CULTIVARS

'Kakegawa AU18' is a distinct variety of *Osteospermum* owing to its ability to flower in hot temperatures, cream/ivory picotee ray floret color and compact growth habit. 'Kakegawa AU18' is most similar to the *Osteospermum* plant named 'Brightside' (U.S. Plant Pat. No. 10,596); however, there are differences as described in the table below (color references are to The Royal Horticultural Society Colour Chart, $4^{th}$ edition):

TABLE 1

| Characteristic | 'Kakegawa AU18' | 'Brightside' |
|---|---|---|
| Ray floret (ligule) color, upper surface: | RHS 155D (white) | Pure white |
| Habit | Upright, Compact | Spreading |

I claim:

1. A new and distinct cultivar of *Osteospermum* plant as shown and described herein.

* * * * *